United States Patent [19]
Haake et al.

[11] Patent Number: 5,658,757
[45] Date of Patent: Aug. 19, 1997

[54] CLONED LEPTOSPIRA OUTER MEMBRANE PROTEIN

[75] Inventors: David A. Haake, Culver City; David R. Blanco, Beverly Hills; Cheryl I. Champion, Culver City; Michael A. Lovett, Los Angeles; James N. Miller, Northridge, all of Calif.

[73] Assignee: The Regents of the University of California, Oakland, Calif.

[21] Appl. No.: 362,739

[22] Filed: Dec. 20, 1994

Related U.S. Application Data

[63] Continuation of Ser. No. 40,747, Mar. 31, 1993, abandoned.
[51] Int. Cl.$^6$ .............................. C12N 15/00; C12N 5/00; C12D 21/06; C07H 19/00
[52] U.S. Cl. ................ 435/69.1; 435/252.3; 435/252.33; 435/320.1; 435/810; 435/325; 435/419; 536/23.7; 536/24.32
[58] Field of Search .......................... 536/23.7, 24.32; 435/69.1, 240.2, 252.3, 252.33, 320.1, 810

[56] References Cited

U.S. PATENT DOCUMENTS

| | | | |
|---|---|---|---|
| 5,091,301 | 2/1992 | Zuerner | 435/6 |
| 5,397,698 | 3/1995 | Goodman et al. | 435/6 |
| 5,401,631 | 3/1995 | Lane et al. | 435/6 |
| 5,466,577 | 11/1995 | Weisburg | 435/6 |
| 5,516,641 | 5/1996 | Ullman et al. | 435/91.1 |

OTHER PUBLICATIONS

Blanchard–Channell et al. "Characterization of *Borrelia coriaceae* Antigens with Monoclonal Antibodies", *Inf. Immun.*59)8):2790–2748 (Aug. 1991).

Allan et al. "Molecular Cloning of the Major Outer Membrane Protein of *Chlamydia trachomatis*", *Inf. Immun.*45(3):637–641 (Sep. 1984).

Haake et al. "Changes in the Surface of *Leptospira interrogans*Serovar Grippotyphosa During In Vitro Cultivation", *Inf. Immun.*59(3):1131–1140 (Mar. 1991).

Van Eys et al. "DNA Hybridization . . . *Leptospira*. . ." *J. Gen. Microbiol.* 134:567–574 (Mar. 1988).

Doherty et al. "Expression of two conserved leptospiral antigens in E. coli" *J. Med. Microbiol.* 28(2):143–150 (1989), in *Biol. Abstr.*87(11):AB–477, #115457 (Jun. 1989).

Richaud et al. "Cloning of Genes for Amino Acid Biosynthesis from Leptospira . . .", *J. Gen. Microbiol.*136:651–656 (Apr. 1990).

Baril et al. "Sizing of the *Leptospira* genome . . ." *Fems Microbiol. Lett.*71: 95–100 (Sep. 1990).

Penn et al. "Genetic Approaches to Cell Biology and Metabolism of Spirochetes ", *Res. Microbiol.* 143: 605–613 (Jul./Aug. 1992).

Yasuda et al. "Deoxyribonucleic Acid Relatedness Between Serogroups and Serovavs in the Family *Leptospiraceae*. . ." *Int. J. Sys. Bact.* 37(4):407–415 (Oct. 1987).

Zuerner et al. "Characterization of Outer Membrane and Secreted Proteins of Leptospira . . ." *Microbial Pathogen.* 10:311–322 (Apr. 1991).

*Primary Examiner*—Vasu S. Jagannathan
*Assistant Examiner*—David Romeo
*Attorney, Agent, or Firm*—Fish & Richardson, P.C.

[57] ABSTRACT

An antigenic preparation is provided which contains a 31 Kd outer membrane protein from Leptospira which can be used immunologically as a vaccine for leptospirosis caused by this organism.

14 Claims, 5 Drawing Sheets

1   GTAGAATTTAGGAACTTTTCAACCTTTTTACGAAAACCTGTTTGACACTAATCTATGAACTTCTAAAGTCCCCCTGT 79

-35                        -10                RBS
80  ATCCGGATTCAAGAGCCAAATACAAATCTTGCCGAAACACAATCAAATTCCAATCGATCGTGAGTAAGGAGTTATCA 158

159 ATG ATC CGT AAC ATA AGT AAG GCA TTG CTC ATT TTA GCC GTA GCA CTA TCT TCG GCT GCA 218
    Met Ile Arg Asn Ile Ser Lys Ala Leu Leu Ile Leu Ala Val Ala Leu Ser Ser Ala Ala

219 AGC CTA AGT GCA AAA ACA TAT GCA ATT GTA GGA TTT GGG TTA CAG TTA GAC CTG GGA CAA 278
    Ser Leu Ser Ala Lys Thr Tyr Ala Ile Val Gly Phe Gly Leu Gln Leu Asp Leu Gly Gln

279 TTA GGA ACC ATC ACT AAA GAC GGT TTG GAC GCT GCG AGT TAT TAT GGT CCA GTC CGA 338
    Leu Gly Thr Ile Thr Lys Asp Gly Leu Asp Ala Ala Ser Tyr Tyr Gly Pro Val Arg

339 TCA ACA GAT ACT TGT ACA GTA GGT CCA AAC GAT CCT ACT TGT GTA CAA AAT CCA GGA AAA 398
    Ser Thr Asp Thr Cys Thr Val Gly Pro Asn Asp Pro Thr Cys Val Gln Asn Pro Gly Lys

399 CCT GCA GGT GAA GGA AAT TAT CTA GGA GTT GCT CCT AGA AAA GCG ATT CCC GCT GAA AAT 458
    Pro Ala Gly Glu Gly Asn Tyr Leu Gly Val Ala Pro Arg Lys Ala Ile Pro Ala Glu Asn

459 AAA TTG ATT ACC CTC GAT AGA ACT ACT GGC GGT TTG ATC AAT GCG AGA AGC ACC AAA GGA 518
    Lys Leu Ile Thr Leu Asp Arg Thr Thr Gly Gly Leu Ile Asn Ala Arg Ser Thr Lys Gly

FIG.1A

519  GCC ATG GTC GGA GGA AAT TTG ATG GTA GGT TAC GAA TCC GAC TTT GGT AAA TAT TTT TTC  578
     Ala Met Val Gly Gly Asn Leu Met Val Gly Tyr Glu Ser Asp Phe Gly Lys Tyr Phe Phe

579  TGG AGA GTT GCT GCA GAA TAT ACT CAA AAA ATT TCC GGT GGT ATT ACA AAA GCG GAC ATC  638
     Trp Arg Val Ala Ala Glu Tyr Thr Gln Lys Ile Ser Gly Gly Ile Thr Lys Ala Asp Ile

639  GCT GGT TAT AGT ATT GTA GAC ATG ACC TGG GGA TTT AGT TCT ATC GTC ATT CCT GCA ACT  698
     Ala Gly Tyr Ser Ile Val Asp Met Thr Trp Gly Phe Ser Ser Ile Val Ile Pro Ala Thr

699  GTT GGT ATT AAA TTG AAT GTT ACT GAA GAC GCT GCT GTG TAT ATG GGA GCC GGT CTG AAC  758
     Val Gly Ile Lys Leu Asn Val Thr Glu Asp Ala Ala Val Tyr Met Gly Ala Gly Leu Asn

759  TAC TTT AAC GGC TGG TGG AGT TTA AAT AAC CTC AAA GGA GGT CAT GAC ATT  818
     Tyr Phe Asn Gly Trp Trp Ser Leu Asn Asn Leu Lys Gly Gly His Asp Ile

819  TTA GCC GCG GGA GCA GCA AGT GTT GCA AAC TTA ATC GCA GAC GGA ACG GAT CCA ATC  878
     Leu Ala Ala Gly Ala Ala Ser Val Ala Asn Leu Ile Ala Asp Gly Thr Asp Pro Ile

879  ACT ACT CGT GAG CAC GTT CGT TTT AGA ACT TCT GGA ATT GCT CCT AAC TTT TTA ATT GGA  938
     Thr Thr Arg Glu His Val Arg Phe Arg Thr Ser Gly Ile Ala Pro Asn Phe Leu Ile Gly

939  ACC CAA GCC AGA GTA ACC GAC AAA GGA CAC GTT TTT CTT GAA TTA GAA ACG ATC ATG TCT  998
     Thr Gln Ala Arg Val Thr Asp Lys Gly His Val Phe Leu Glu Leu Glu Thr Ile Met Ser

FIG.1B

```
 999 GCT GCG TAT GCA GTT GGT AAA ACT CAA TCT GCT GGA GCC ACG AAT CTT TCT CCT TTT 1058
     Ala Ala Tyr Ala Val Gly Lys Thr Gln Ser Ala Gly Ala Thr Asn Leu Ser Pro Phe

1059 CCA GCG TAT CCG ATC GTT GTC GGT GGG CAA ATC TAC AGA TTC GGT TAT AAA CAC GAA CTC 1118
     Pro Ala Tyr Pro Ile Val Val Gly Gly Gln Ile Tyr Arg Phe Gly Tyr Lys His Glu Leu

1119 TAAGGTTCAAATCAATAATAACGATTTCTAATTAAAAAGGCTCTCTTTTAGAGAGCCTTTTTATTTTCTAAACCT 1197
          *                                     <------------->
                       <------------->

1198 GTTCTTATAACCTATCAACGACTATTTCTAAAGCAGTTTTTATAAATATAATTATATTAAAAAATTTTTATGCCTTTG 1276
```

FIG.1C

```
TMS         ****        ****       ****  ****    *****   ****   *****          *****           ****
                        #6          #7     #8      #9                           #11             #16

Nmp1        VSVRYDS..FSGFSGSVQF..YYAGLNY..FAGNYAFKY..AKGTDPL..NLALAAQLDL..AASVGLRHKF
            :.!::    :..!..:.:    !!!!    !.!..:.   !!!!    !:.::.!..   ..:.!.!..
OmpL1       LMVGYES..YFFWRVAAEY..MGAGLNY..FNGWSLNG..ADGTDPI..NFLIGTQARV..IYRFGYKHEL
```

FIG.2

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 963 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: OMP L1

( i x ) FEATURE:
        ( A ) NAME/KEY: CDS
        ( B ) LOCATION: 1..963

( x i ) SEQUENCE DESCRIPTION: SEQ ID NO:1:

```
ATG  ATC  CGT  AAC  ATA  AGT  AAG  GCA  TTG  CTC  ATT  TTA  GCC  GTA  GCA  CTA        48
Met  Ile  Arg  Asn  Ile  Ser  Lys  Ala  Leu  Leu  Ile  Leu  Ala  Val  Ala  Leu
 1                    5                         10                       15

TCT  TCG  GCT  GCA  AGC  CTA  AGT  GCA  AAA  ACA  TAT  GCA  ATT  GTA  GGA  TTT        96
Ser  Ser  Ala  Ala  Ser  Leu  Ser  Ala  Lys  Thr  Tyr  Ala  Ile  Val  Gly  Phe
                     20                         25                       30

GGG  TTA  CAG  TTA  GAC  CTG  GGA  CAA  TTA  GGA  GGA  ACC  ATC  ACT  AAA  GAC       144
Gly  Leu  Gln  Leu  Asp  Leu  Gly  Gln  Leu  Gly  Gly  Thr  Ile  Thr  Lys  Asp
               35                         40                       45

GGT  TTG  GAC  GCT  GCG  AGT  TAT  TAT  GGT  CCA  GTC  CGA  TCA  ACA  GAT  ACT       192
Gly  Leu  Asp  Ala  Ala  Ser  Tyr  Tyr  Gly  Pro  Val  Arg  Ser  Thr  Asp  Thr
         50                         55                       60

TGT  ACA  GTA  GGT  CCA  AAC  GAT  CCT  ACT  TGT  GTA  CAA  AAT  CCA  GGA  AAA       240
Cys  Thr  Val  Gly  Pro  Asn  Asp  Pro  Thr  Cys  Val  Gln  Asn  Pro  Gly  Lys
 65                   70                         75                       80
```

| | | | | | | | | | | | | | | | | |
|---|---|---|---|---|---|---|---|---|---|---|---|---|---|---|---|---|
| CCT | GCA | GGT | GAA | GGA | AAT | TAT | CTA | GGA | GTT | GCT | CCT | AGA | AAA | GCG | ATT | 288 |
| Pro | Ala | Gly | Glu | Gly | Asn | Tyr | Leu | Gly | Val | Ala | Pro | Arg | Lys | Ala | Ile | |
| | | | | 85 | | | | | 90 | | | | 95 | | | |
| CCC | GCT | GAA | AAT | AAA | TTG | ATT | ACC | CTC | GAT | AGA | ACT | ACT | GGC | GGT | TTG | 336 |
| Pro | Ala | Glu | Asn | Lys | Leu | Ile | Thr | Leu | Asp | Arg | Thr | Thr | Gly | Gly | Leu | |
| | | | 100 | | | | 105 | | | | 110 | | | | | |
| ATC | AAT | GCG | AGA | AGC | ACC | AAA | GGA | GCC | ATG | GTC | GGA | GGA | AAT | TTG | ATG | 384 |
| Ile | Asn | Ala | Arg | Ser | Thr | Lys | Gly | Ala | Met | Val | Gly | Gly | Asn | Leu | Met | |
| | | 115 | | | | 120 | | | | | 125 | | | | | |
| GTA | GGT | TAC | GAA | TCC | GAC | TTT | GGT | AAA | TAT | TTT | TTC | TGG | AGA | GTT | GCT | 432 |
| Val | Gly | Tyr | Glu | Ser | Asp | Phe | Gly | Lys | Tyr | Phe | Phe | Trp | Arg | Val | Ala | |
| | | 130 | | | | 135 | | | | 140 | | | | | | |
| GCA | GAA | TAT | ACT | CAA | AAA | ATT | TCC | GGT | GGT | ATT | ACA | AAA | GCG | GAC | ATC | 480 |
| Ala | Glu | Tyr | Thr | Gln | Lys | Ile | Ser | Gly | Gly | Ile | Thr | Lys | Ala | Asp | Ile | |
| 145 | | | | | 150 | | | | 155 | | | | | 160 | | |
| GCT | GGT | TAT | AGT | ATT | GTA | GAC | ATG | ACC | TGG | GGA | TTT | AGT | TCT | ATC | GTC | 528 |
| Ala | Gly | Tyr | Ser | Ile | Val | Asp | Met | Thr | Trp | Gly | Phe | Ser | Ser | Ile | Val | |
| | | | | 165 | | | | | 170 | | | | | 175 | | |
| ATT | CCT | GCA | ACT | GTT | GGT | ATT | AAA | TTG | AAT | GTT | ACT | GAA | GAC | GCT | GCT | 576 |
| Ile | Pro | Ala | Thr | Val | Gly | Ile | Lys | Leu | Asn | Val | Thr | Glu | Asp | Ala | Ala | |
| | | | 180 | | | | 185 | | | | | 190 | | | | |
| GTG | TAT | ATG | GGA | GCC | GGT | CTG | AAC | TAC | TTT | AAC | GGC | TGG | TGG | AGT | TTA | 624 |
| Val | Tyr | Met | Gly | Ala | Gly | Leu | Asn | Tyr | Phe | Asn | Gly | Trp | Trp | Ser | Leu | |
| | | 195 | | | | 200 | | | | | 205 | | | | | |
| AAC | GGA | TCC | AAT | AAC | CTC | AAA | GGA | GGT | CAT | GAC | ATT | TTA | GCC | GCA | GCG | 672 |
| Asn | Gly | Ser | Asn | Asn | Leu | Lys | Gly | Gly | His | Asp | Ile | Leu | Ala | Ala | Ala | |
| | 210 | | | | | 215 | | | | | 220 | | | | | |
| GGA | GCA | GGA | AGT | GTT | GCA | AAC | TTA | ATC | GCA | GAC | GGA | ACG | GAT | CCA | ATC | 720 |
| Gly | Ala | Gly | Ser | Val | Ala | Asn | Leu | Ile | Ala | Asp | Gly | Thr | Asp | Pro | Ile | |
| 225 | | | | 230 | | | | | 235 | | | | | 240 | | |
| ACT | ACT | CGT | GAG | CAC | GTT | CGT | TTT | AGA | ACT | TCT | GGA | ATT | GCT | CCT | AAC | 768 |
| Thr | Thr | Arg | Glu | His | Val | Arg | Phe | Arg | Thr | Ser | Gly | Ile | Ala | Pro | Asn | |
| | | | | 245 | | | | | 250 | | | | | 255 | | |
| TTT | TTA | ATT | GGA | ACC | CAA | GCC | AGA | GTA | ACC | GAC | AAA | GGA | CAC | GTT | TTT | 816 |
| Phe | Leu | Ile | Gly | Thr | Gln | Ala | Arg | Val | Thr | Asp | Lys | Gly | His | Val | Phe | |
| | | | 260 | | | | | 265 | | | | | 270 | | | |
| CTT | GAA | TTA | GAA | ACG | ATC | ATG | TCT | GCT | GCG | TAT | GCA | GTT | GGT | AAA | ACT | 864 |
| Leu | Glu | Leu | Glu | Thr | Ile | Met | Ser | Ala | Ala | Tyr | Ala | Val | Gly | Lys | Thr | |
| | | 275 | | | | | 280 | | | | | 285 | | | | |
| CAA | TCT | GCT | GGA | GGA | GCC | ACG | AAT | CTT | TCT | CCT | TTT | CCA | GCG | TAT | CCG | 912 |
| Gln | Ser | Ala | Gly | Gly | Ala | Thr | Asn | Leu | Ser | Pro | Phe | Pro | Ala | Tyr | Pro | |
| | 290 | | | | | 295 | | | | | 300 | | | | | |
| ATC | GTT | GTC | GGT | GGG | CAA | ATC | TAC | AGA | TTC | GGT | TAT | AAA | CAC | GAA | CTC | 960 |
| Ile | Val | Val | Gly | Gly | Gln | Ile | Tyr | Arg | Phe | Gly | Tyr | Lys | His | Glu | Leu | |
| 305 | | | | 310 | | | | | 315 | | | | | 320 | | |
| TAA | | | | | | | | | | | | | | | | 963 |

( 2 ) INFORMATION FOR SEQ ID NO:2:

( i ) SEQUENCE CHARACTERISTICS:
        ( A ) LENGTH: 320 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ile | Arg | Asn | Ile | Ser | Lys | Ala | Leu | Leu | Ile | Leu | Ala | Val | Ala | Leu |
| 1 | | | | 5 | | | | | 10 | | | | | 15 | |
| Ser | Ser | Ala | Ala | Ser | Leu | Ser | Ala | Lys | Thr | Tyr | Ala | Ile | Val | Gly | Phe |
| | | | 20 | | | | | 25 | | | | | 30 | | |

```
Gly Leu Gln Leu Asp Leu Gly Gln Leu Gly Gly Thr Ile Thr Lys Asp
        35                  40                  45

Gly Leu Asp Ala Ala Ser Tyr Tyr Gly Pro Val Arg Ser Thr Asp Thr
        50                  55                  60

Cys Thr Val Gly Pro Asn Asp Pro Thr Cys Val Gln Asn Pro Gly Lys
65                      70                  75                  80

Pro Ala Gly Glu Gly Asn Tyr Leu Gly Val Ala Pro Arg Lys Ala Ile
                85                  90                      95

Pro Ala Glu Asn Lys Leu Ile Thr Leu Asp Arg Thr Thr Gly Gly Leu
            100                 105                 110

Ile Asn Ala Arg Ser Thr Lys Gly Ala Met Val Gly Gly Asn Leu Met
            115                 120                 125

Val Gly Tyr Glu Ser Asp Phe Gly Lys Tyr Phe Phe Trp Arg Val Ala
    130                 135                 140

Ala Glu Tyr Thr Gln Lys Ile Ser Gly Gly Ile Thr Lys Ala Asp Ile
145                 150                 155                 160

Ala Gly Tyr Ser Ile Val Asp Met Thr Trp Gly Phe Ser Ser Ile Val
                165                 170                 175

Ile Pro Ala Thr Val Gly Ile Lys Leu Asn Val Thr Glu Asp Ala Ala
            180                 185                 190

Val Tyr Met Gly Ala Gly Leu Asn Tyr Phe Asn Gly Trp Trp Ser Leu
        195                 200                 205

Asn Gly Ser Asn Asn Leu Lys Gly Gly His Asp Ile Leu Ala Ala Ala
    210                 215                 220

Gly Ala Gly Ser Val Ala Asn Leu Ile Ala Asp Gly Thr Asp Pro Ile
225                 230                 235                 240

Thr Thr Arg Glu His Val Arg Phe Arg Thr Ser Gly Ile Ala Pro Asn
            245                 250                 255

Phe Leu Ile Gly Thr Gln Ala Arg Val Thr Asp Lys Gly His Val Phe
            260                 265                 270

Leu Glu Leu Glu Thr Ile Met Ser Ala Ala Tyr Ala Val Gly Lys Thr
        275                 280                 285

Gln Ser Ala Gly Gly Ala Thr Asn Leu Ser Pro Phe Pro Ala Tyr Pro
    290                 295                 300

Ile Val Val Gly Gly Gln Ile Tyr Arg Phe Gly Tyr Lys His Glu Leu
305                 310                 315                 320
```

( 2 ) INFORMATION FOR SEQ ID NO:3:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..14

( x i ) SEQUENCE DESCRIPTION: SEQ ID NO:3:

```
Lys Thr Tyr Ala Ile Val Gly Phe Gly Leu Gln Leu Asp Asn
1               5                   10
```

( 2' ) INFORMATION FOR SEQ ID NO:4:

( i ) SEQUENCE CHARACTERISTICS:
        ( A ) LENGTH: 20 base pairs (B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..20

(xi) SEQUENCE DESCRIPTION: SEQ ID NO:4:

AARACNTA Y G  CNATHGTNGG       20

(2) INFORMATION FOR SEQ ID NO:5:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..20

(xi) SEQUENCE DESCRIPTION: SEQ ID NO:5:

TT Y GGN Y TDC  AR Y TD-GA Y AA       20

(2) INFORMATION FOR SEQ ID NO:6:

(i) SEQUENCE CHARACTERISTICS:
(A) LENGTH: 60 amino acids
(B) TYPE: amino acid
(C) STRANDEDNESS: single
(D) TOPOLOGY: linear (ii) MOLECULE TYPE: peptide (vii) IMMEDIATE SOURCE:
(B) CLONE: Nmp1

(ix) FEATURE:
(A) NAME/KEY: Peptide
(B) LOCATION: 1..60

(xi) SEQUENCE DESCRIPTION: SEQ ID NO:6:

| Val | Ser | Val | Arg | Tyr | Asp | Ser | Phe | Ser | Gly | Phe | Ser | Gly | Ser | Val | Gln |
| 1 | | | | 5 | | | | | 10 | | | | | 15 | |
| Phe | Tyr | Tyr | Ala | Gly | Leu | Asn | Tyr | Phe | Ala | Gly | Asn | Tyr | Ala | Phe | Lys |
| | | | 20 | | | | 25 | | | | | 30 | | | |
| Tyr | Ala | Lys | Gly | Thr | Asp | Pro | Leu | Asn | Leu | Ala | Leu | Ala | Ala | Gln | Leu |
| | | 35 | | | | 40 | | | | | 45 | | | | |
| Asp | Leu | Ala | Ala | Ser | Val | Gly | Leu | Arg | His | Lys | Phe | | | | |
| | 50 | | | | 55 | | | | | 60 | | | | | |

(2) INFORMATION FOR SEQ ID NO:7:

(i) SEQUENCE CHARACTERISTICS:
(A) LENGTH: 60 amino acids
(B) TYPE: amino acid
(C) STRANDEDNESS: single
(D) TOPOLOGY: linear (ii) MOLECULE TYPE: peptide (vii) IMMEDIATE SOURCE:
(B) CLONE: PepL ( i x ) FEATURE:
 ( A ) NAME/KEY: Peptide
 ( B ) LOCATION: 1..60

( x i ) SEQUENCE DESCRIPTION: SEQ ID NO:7:

```
Leu Met Val Gly Tyr Glu Ser Tyr Phe Phe Trp Arg Val Ala Ala Glu
 1           5                   10                      15

Tyr Met Gly Ala Gly Leu Asn Tyr Phe Asn Gly Trp Trp Ser Leu Asn
             20                  25                  30

Gly Ala Asp Gly Thr Asp Pro Ile Asn Phe Leu Ile Gly Thr Gln Ala
         35              40                      45

Arg Val Ile Tyr Arg Phe Gly Tyr Lys His Glu Leu
     50                  55                  60
```

CLONED LEPTOSPIRA OUTER MEMBRANE PROTEIN

This is a continuation of application Ser. No. 08/040,747 filed on Mar. 31, 1993, now abandoned.

This invention was made with government support under Grant Number AI-21352 by the National Institute of Health. The government has certain rights in the invention.

BACKGROUND OF THE INVENTION

1. Field of the Invention

This invention relates generally to an antigenic preparation and specifically to a Leptospira outer membrane protein (OmpL1) which is used to induce a protective immune response in animals. Such a protein can be used immunologically as a vaccine for leptospirosis caused by this organism. Alternatively, diagnosis of leptospirosis can be performed by detecting the presence of the protein, antibody to the protein, or polynucleotide which encodes the protein.

2. Description of Related Art

Leptospirosis is a widespread zoonotic disease caused by pathogenic strains of Leptospira which are capable of infecting most mammalian species. At present, there are six pathogenic species and three nonpathogenic species within the genus Leptospira. Infection occurs either through direct contact with an infected animal or indirect contact with contaminated soil or water. In livestock, the disease causes economic losses due to abortion, stillbirth, infertility, decreased milk production, and death.

Efforts to control leptospirosis have been hampered because virulent leptospires have the capacity for both long-term survival in the environment as well as persistent infection and shedding by wildlife and livestock. Currently available leptospiral vaccines produce short-term immunity and do not provide cross-protection against many of the 170 serovars of pathogenic Leptospira (Thiermann, et al, *J. Am. Vet. Med. Assoc.* 184:722, 1984). These vaccines consist of inactivated whole organisms or outer envelope preparations which produce seroreactivity as determined by microscopic agglutination of intact organisms. The nature of the protective immunogens in these vaccine preparations has not been conclusively elucidated, although several lines of evidence suggest that lipopolysaccharide-like substance (LLS) may confer a degree of protection.

The pathogenesis of leptospirosis is very similar to that of other spirochetal diseases, including syphilis (caused by *Treponema pallidum*) and Lyme borreliosis (caused by *Borrelia burgdorferi*). Both syphilis and Lyme borreliosis are characterized by widespread dissemination early in the course of disease, including invasion of the central nervous system. Leptospira share this ability with other pathogenic spirochetes such that meningitis is a common manifestation of leptospirosis. Another feature of spirochetal infections is the ability to persist chronically in the host, as manifested in cases of tertiary syphilis and chronic Lyme arthritis.

In attempting to identify leptospiral outer membrane proteins (OMPs), previous research was unsuccessful due to such problems as: 1) the techniques used to identify surface-exposed proteins probably involved damage to the fragile leptospiral outer membrane resulting in exposure of subsurface structures; 2) putative surface-exposed proteins that were identified included a 35-36 kD doublet corresponding to Leptospira endoflagella (Kelson, et al., *J. Med. Microbiol.* 26:47, 1988), which are subsurface structures in spirochetes; and 3) use of SDS which nonselectively solubilizes proteins irrespective of their native cellular location.

Nunes-Edwards, et al. (*Infect. Immun.* 48:492, 1985) introduced the use of radioimmunoprecipitation and cell fractionation schemes based on the use of SDS in an effort to identify leptospiral OMPs. The leptospires used in their radioimmunoprecipitation procedure were subjected to high speed centrifugation (20,000×g) prior to the addition of antibody. Such high centrifugal forces cause mechanical disruption of the leptospiral outer membrane. Niikura, et al. (*Zbl. Bakt. Hyg. A.* 266:453, 1987) immunoprecipitated SDS-solubilized extracts of virulent and avirulent strains of *L. interrogans* serovar copenhageni that had been labeled by lactoperoxidase-catalyzed surface radioiodination. Since both of these studies precipitated a 35–36 kD doublet consistent with leptospiral endoflagella, there was a concern as to whether the other proteins identified might also have a subsurface rather than a surface location.

Jost, et al. (*J. Med. Microbiol.* 27:143) characterized a monoclonal antibody with specificity for a 35 kD proteinase K sensitive antigen which was present in a leptospiral outer envelope preparation. However, to demonstrate binding of the monoclonal antibody by immunoelectron microscopy, the leptospiral outer membrane had to be disrupted. Doherty, et al (*J. Med. Microbiol.* 28:143) cloned two leptospiral proteins represented in an SDS-generated outer membrane preparation of *L. interrogans*, but did not provide corroborating evidence that these proteins are either constituents of the outer membrane or are surface-exposed.

Unsuccessful research on the identification of Leptospira and *T. pallidum* OMPs has shown the importance of taking into account spirochetal outer membrane fragility and the lack of outer membrane selectivity of ionic detergents such as sodium dodecyl sulfate (SDS) (Cunningham, et al, *J. Bacteriol.* 170:5789, 1988; Penn, et al., *J. Gen. Microbiol.* 131:2349, 1985; Stamm, et al., *Infect. Immun.* 55:2255, 1987). Outer membrane proteins are of great importance because they play a key role in bacterial pathogenesis. The identification of outer membrane proteins involved in Leptospira pathogenesis is significant to understanding not only leptospiral outer membrane proteins and their involvement in pathogenesis, but also to understanding other spirochetal outer membrane proteins and their role in pathogenesis.

SUMMARY OF THE INVENTION

The present invention is based on the identification of OmpL1 as a major leptospiral outer membrane protein which is associated with pathogenic strains of Leptospira. Due to spirochetal outer membrane fragility and the fact that outer membrane proteins are present in small amounts, there have been no definitive reports of membrane spanning spirochetal outer membrane proteins until the present invention. The invention describes a 31 kD outer membrane protein from Leptospira and the gene encoding the protein. This gene is present in all species of pathogenic Leptospira tested and is absent in all nonpathogenic Leptospira tested. The deduced amino acid sequence has a typical leader peptidase I cleavage site, implying export beyond the inner membrane. The 31 kD protein has been designated OmpL1 for outer membrane protein of Leptospira. This immunogenic polypeptide is useful for inducing an immune response to pathogenic Leptospira as well as providing a diagnostic target for leptospirosis.

BRIEF DESCRIPTION OF THE DRAWINGS

FIG. 1 shows the DNA sequence and deduced amino acid sequence of OmpL1.

FIG. 2 shows a comparison between Nmp1 (an outer membrane protein porin of *Neisseria meningitidis*) and OmpL1 amino acid sequences.

DETAILED DESCRIPTION OF THE INVENTION

Figure 3A:
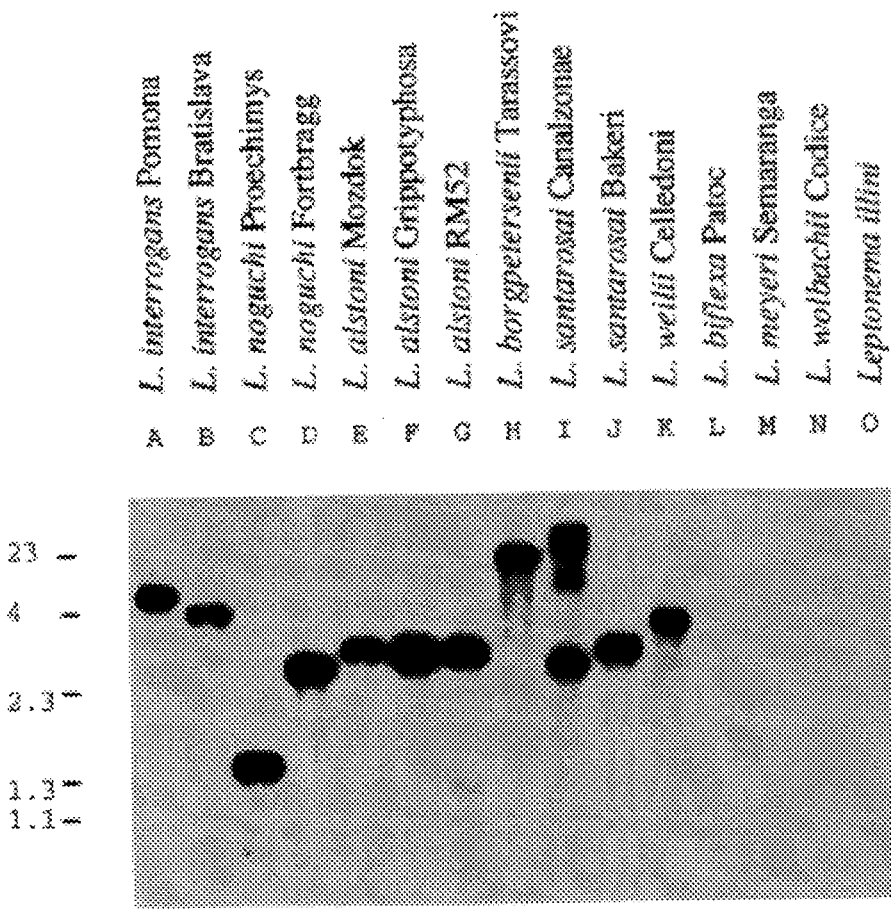
FIG. 3A shows a Southern blot using ompL1 as a probe to detect the gene in pathogenic and non-pathogenic Leptospira (medium stringency).

The present invention provides an isolated immunogenic polypeptide from an outer membrane protein of a pathogenic Leptospira species. Also included is a polynucleotide sequence which encodes the polypeptide. The outer membrane protein is a 31 kD protein originally isolated from Leptospira alstoni which has been termed OmpL1 and is a pathogen-associated exported protein of Leptospira. This immunogenic polypeptide is useful in a pharmaceutical composition for inducing an immune response to pathogenic Leptospira.

The invention includes a method of producing the polypeptide portion of an outer membrane protein of Leptospira using recombinant DNA techniques. The gene for the L. alstoni OmpL1 outer membrane protein was cloned into a plasmid vector which was then used to transform E. coli. When the OmpL1 gene was expressed in E. coli, the polypeptide produced had a molecular weight of approximately 31 kD as determined by SDS-polyacrylamide gel electrophoresis. Reactivity to the 31 kD protein was demonstrated with antisera to pathogenic strains of Leptospira including L. interrogans serovars icterohaemorrhagiae, pomona and bratislava, L. alstoni, serovars grippotyphosa and fortbragg, L. santarosai, serovars bakeri and canalzonae, and L. weilii, serovar celledoni. This indicates that OmpL1 is not only expressed, but also antigenically conserved among pathogenic Leptospira regardless of species and, therefore, this polypeptide is an excellent vaccine candidate as well as a marker antigen for diagnosis of leptospirosis.

Extraction of proteins from whole cells of L. alstoni using nonionic detergent Triton X-114 (TX-114), resulted in the solubilization of a number of proteins, including a detergent phase protein of 31 kD (OmpL1). Surface immunoprecipitation using antiserum raised to whole L. alstoni, was used to generate a fraction which was subjected to SDS-polyacrylamide gel electrophoresis. The electrophoresed fraction was then transferred to a sequencing membrane and an N-terminal sequence of 14 amino acids of the 31 kD protein was determined. Based upon the N-terminal amino acid sequence, two degenerate oligonucleotide probes were synthesized. An L. alstoni genomic DNA library was probed with the oligonucleotides and a 2.5 kb insert was identified as containing the coding sequence for 31 kD OmpL1.

Sequence analysis showed that the OmpL1 structural gene consists of 960 bases encoding a protein of 320 amino acids. As expected for proteins to be exported beyond the inner membrane, the derived amino acid sequence begins with a 24-residue signal peptide. The OmpL1 sequence contains ten stretches of amphipathic beta-sheet structure, consistent with outer membrane protein transmembrane segments. Southern hybridization studies showed that there is a strong correlation between Leptospira pathogenicity and the presence of the OmpL1 gene. A single copy of the OmpL1 gene was present in all strains of pathogenic Leptospira tested, and absent in all nonpathogenic strains of Leptospira tested.

The bacterial genes for the OmpL1 outer membrane protein can be derived from any strain of pathogenic Leptospira. Preferably the protein is from Leptospira alstoni, serovar grippotyphosa.

The invention provides polynucleotides encoding the Leptospira OmpL1 protein. These polynucleotides include DNA and RNA sequences which encode the protein. It is understood that all polynucleotides encoding all or a portion of OmpL1 are also included herein, so long as the encoded portions exhibit the function of OmpL1, such as the ability to induce or bind antibody. Such polynucleotides include both naturally occurring and intentionally manipulated, for example, mutagenized polynucleotides.

DNA sequences of the invention can be obtained by several methods. For example, the DNA can be isolated using hybridization procedures which are well known in the art. These include, but are not limited to: 1) hybridization of probes to genomic libraries to detect shared nucleotide sequences and 2) antibody screening of expression libraries to detect shared structural features.

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. By using stringent hybridization conditions directed to avoid non-specific binding, it is possible, for example, to allow the autoradiographic visualization of a specific DNA clone by the hybridization of the target DNA to that single probe in the mixture which is its complete complement (Wallace, et al., Nucleic Acid Research, 9:879, 1981).

Alternatively, an expression library can be screened indirectly for OmpL1 peptides having at least one epitope using antibodies to OmpL1. Such antibodies can be either polyclonally or monoclonally derived and used to detect expression product indicative of the presence of OmpL1 DNA. Generally, a lambda gt11 library is constructed and screened immunologically according to the method of Huynh, et al. (in DNA Cloning: A Practical Approach, D. M. Glover, ed., 1:49, 1985).

The development of specific DNA sequences encoding OmpL1 can also be obtained by: (1) isolation of a double-stranded DNA sequence from the genomic DNA, and (2) chemical manufacture of a DNA sequence to provide the necessary codons for the polypeptide of interest.

DNA sequences encoding OmpL1 can be expressed in vitro by DNA transfer into a suitable host cell. "Recombinant host cells" or "host cells" are cells in which a vector can be propagated and its DNA expressed. The term also includes any progeny of the subject host cell. It is understood that not all progeny are identical to the parental cell since there may be mutations that occur at replication. However, such progeny are included when the terms above are used.

The term "host cell" as used in the present invention is meant to include not only prokaryotes, but also, such eukaryotes as yeasts, filamentous fungi, as well as plant and animal cells. The term "prokaryote" is meant to include all bacteria which can be transformed with the gene for the expression of the OmpL1 outer membrane protein of Leptospira. Prokaryotic hosts may include Gram negative as well as Gram positive bacteria, such as E. coli, S. typhimurium, and Bacillus subtilis.

A recombinant DNA molecule coding for the OmpL1 protein can be used to transform a host using any of the techniques commonly known to those of ordinary skill in the art. Especially preferred is the use of a plasmid containing the OmpL1 coding sequence for purposes of prokaryotic transformation. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell.

In the present invention, the OmpL1 sequences may be inserted into a recombinant expression vector. The term "recombinant expression vector" refers to a plasmid, virus or other vehicle known in the art that has been manipulated by insertion or incorporation of OmpL1 genetic sequences. Such expression vectors contain a promotor sequence which facilitates the efficient transcription of the inserted genetic sequence in the host. The expression vector typically contains an origin of replication, a promoter, as well as specific genes which allow phenotypic selection of the transformed cells. The transformed prokaryotic hosts can be cultured according to means known in the art to achieve optimal cell growth. Various shuttle vectors for the expression of foreign genes in yeast have been reported (Heinemann, et al., *Nature*, 340:205, 1989; Rose, et al., *Gene*, 60:237, 1987). Biologically functional DNA vectors capable of expression and replication in a host are known in the art. Such vectors are used to incorporate DNA sequences of the invention.

Methods for preparing fused, operably linked genes and expressing them in bacteria are known and are shown, for example, in U.S. Pat. No. 4,366,246 which is incorporated herein by reference. The genetic constructs and methods described therein can be utilized for expression of Leptospira OmpL1 in prokaryotic hosts.

Examples of promoters which can be used in the invention are: rec A, trp, lac, tac, and bacteriophage lambda $p_R$ or $p_L$. Examples of plasmids which can be used in the invention are listed in Maniatis, et al., (*Molecular Cloning*, Cold Spring Harbor Laboratories, 1982).

Antibodies provided in the present invention are immunoreactive with OmpL1 protein. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature*, 256:495, 1975; *Current Protocols in Molecular Biology*, Ausubel, et al., ed., 1989). The term antibody, or immunoglobulin, as used in this invention includes intact molecules as well as fragments thereof, such as Fab and $F(ab')_2$, which are capable of binding an epitopic determinant on OmpL1.

Minor modifications of OmpL1 primary amino acid sequence may result in proteins which have substantially equivalent function compared to the OmpL1 protein described herein. Such modifications may be deliberate, as by site-directed mutagenesis, or may be spontaneous. All proteins produced by these modifications are included herein as long as OmpL1 function exists.

Modifications of OmpL1 primary amino acid sequence also include conservative variations. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Isolation and purification of microbially expressed protein, on fragments thereof, provided by the invention, may be carried out by conventional means including preparative chromatography and immunological separations involving monoclonal or polyclonal antibodies.

The invention extends to any host modified according to the methods described, or modified by any other methods, commonly known to those of ordinary skill in the art, such as, for example, by transfer of genetic material using a lysogenic phage, and which result in a prokaryote expressing the Leptospira gene for OmpL1 protein. Prokaryotes transformed with the Leptospira gene encoding the OmpL1 protein are particularly useful for the production of polypeptides which can be used for the immunization of an animal.

In one embodiment, the invention provides a pharmaceutical composition useful for inducing an immune response to pathogenic Leptospira in an animal comprising an immunologically effective amount of OmpL1 in a pharmaceutically acceptable carrier. The term "immunogenically effective amount," as used in describing the invention, is meant to denote that amount of Leptospira antigen which is necessary to induce in an animal the production of an immune response to Leptospira. The OmpL1 outer membrane protein of the invention is particularly useful in sensitizing the immune system of an animal such that, as one result, an immune response is produced which ameliorates the effect of Leptospira infection.

The OmpL1 outer membrane protein can be administered parenterally by injection, rapid infusion, nasopharyngeal absorption, dermal absorption, and orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable forms for suspending the liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, and sweetening, flavoring, and perfuming agents.

It is also possible for the antigenic preparations containing the OmpL1 protein of the invention to include an adjuvant. Adjuvants are substances that can be used to nonspecifically augment a specific immune response. Normally, the adjuvant and the antigen are mixed prior to presentation to the immune system, or presented separately, but into the same site of the animal being immunized. Adjuvants can be loosely divided into several groups based on their composition. These groups include oil adjuvants (for example, Freund's Complete and Incomplete), mineral salts (for example, $AlK(SO_4)_2$, $AlNa(SO_4)_2$, $AlNH_4(SO_{04})$, silica, alum, $Al(OH)_3$, $Ca_3(PO_4)_2$, kaolin, and carbon), polynucleotides (for example, poly IC and poly AU acids), and certain natural substances (for example, wax D from *Mycobacterium tuberculosis*, as well as substances found in *Corynebacterium parvum, Bordetella pertussis,* and members of the genus Brucella).

In another embodiment, a method of inducing an immune response to pathogenic Leptospira in animal is provided. Many different techniques exist for the timing of the immunizations when a multiple immunization regimen is utilized. It is possible to use the antigenic preparation of the invention more than once to increase the levels and diversity of expression of the immune response of the immunized animal. Typically, if multiple immunizations are given, they will be spaced two to four weeks apart. Subjects in which an immune response to Leptospira is desirable include swine, cattle and humans.

Generally, the dosage of OmpL1 protein administered to an animal will vary depending on such factors as age, condition, sex and extent of disease, if any, and other variables which can be adjusted by one of ordinary skill in the art.

The antigenic preparations of the invention can be administered as either single or multiple dosages and can vary from about 10 ug to about 1,000 ug for the Leptospira OmpL1 antigen per dose, more preferably from about 50 ug to about 700 ug OmpL1 antigen per dose, most preferably from about 50 ug to about 300 ug OmpL1 antigen per dose.

When used for immunotherapy, the monoclonal antibodies of the invention may be unlabeled or labeled with a therapeutic agent. These agents can be coupled either directly or indirectly to the monoclonal antibodies of the invention. One example of indirect coupling is by use of a spacer moiety. These spacer moieties, in turn, can be either insoluble or soluble (Diener, et al., *Science,* 231:148, 1986) and can be selected to enable drug release from the monoclonal antibody molecule at the target site. Examples of therapeutic agents which can be coupled to the monoclonal antibodies of the invention for immunotherapy are drugs, radioisotopes, lectins, and toxins.

The labeled or unlabeled monoclonal antibodies of the invention can also be used in combination with therapeutic agents such as those described above. Especially preferred are therapeutic combinations comprising the monoclonal antibody of the invention and immunomodulators and other biological response modifiers.

When the monoclonal antibody of the invention is used in combination with various therapeutic agents, such as those described herein, the administration of the monoclonal antibody and the therapeutic agent usually occurs substantially contemporaneously. The term "substantially contemporaneously" means that the monoclonal antibody and the therapeutic agent are administered reasonably close together with respect to time. Usually, it is preferred to administer the therapeutic agent before the monoclonal antibody. For example, the therapeutic agent can be administered 1 to 6 days before the monoclonal antibody. The administration of the therapeutic agent can be daily, or at any other interval, depending upon such factors, for example, as the nature of the disorder, the condition of the patient and half-life of the agent.

The dosage ranges for the administration of monoclonal antibodies of the invention are those large enough to produce the desired effect in which the onset symptoms of the leptospiral disease are ameliorated. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician in the event of any complication. Dosage can vary from about 0.1 mg/kg to about 2000 mg/kg, preferably about 0.1 mg/kg to about 500 mg/kg, in one or more dose administrations daily, for one or several days. Generally, when the monoclonal antibodies of the invention are administered conjugated with therapeutic agents, lower dosages, comparable to those used for in vivo diagnostic imaging, can be used.

The monoclonal antibodies of the invention can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

In a further embodiment, the invention provides a method of detecting a pathogenic Leptospira-associated disorder in a subject comprising contacting a cell component with a reagent which binds to the cell component. The cell component can be nucleic acid, such as DNA or RNA, or it can be protein. When the component is nucleic acid, the reagent is a nucleic acid probe or PCR primer. When the cell component is protein, the reagent is an antibody probe. The probes are detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

For purposes of the invention, an antibody or nucleic acid probe specific for OmpL1 may be used to detect the presence of OmpL1 polypeptide (using antibody) or polynucleotide (using nucleic acid probe) in biological fluids or tissues. Any specimen containing a detectable amount of OmpL1 antigen or polynucleotide can be used. A preferred specimen of this invention is blood, urine, cerebrospinal fluid, or tissue of endothelial origin.

When the cell component is nucleic acid, it may be necessary to amplify the nucleic acid prior to binding with a Leptospira specific probe. Preferably, polymerase chain reaction (PCR) is used, however, other nucleic acid amplification procedures such as ligase chain reaction (LCR), ligated activated transcription (LAT) and nucleic acid sequence-based amplification (NASBA) may be used.

Another technique which may also result in greater sensitivity consists of coupling antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific antihapten antibodies.

Alternatively, OmpL1 polypeptide can be used to detect antibodies to OmpL1 polypeptide in a specimen. The OmpL1 of the invention is particularly suited for use in immunoassays in which it can be utilized in liquid phase or bound to a solid phase carrier. In addition, OmpL1 used in these assays can be detectably labeled in various ways.

Examples of immunoassays which can utilize the OmpL1 of the invention are competitive and noncompetitive immunoassays in either a direct or indirect format. Examples of such immunoassays are the radioimmunoassay (RIA), the sandwich (immunometric assay) and the Western blot assay. Detection of antibodies which bind to the OmpL1 of the invention can be done utilizing immunoassays which run in either the forward, reverse, or simultaneous modes, including immunohistochemical assays on physiological samples. The concentration of OmpL1 which is used will vary depending on the type of immunoassay and nature of the detectable label which is used. However, regardless of the type of immunoassay which is used, the concentration of OmpL1 utilized can be readily determined by one of ordinary skill in the art using routine experimentation.

The OmpL1 of the invention can be bound to many different carriers and used to detect the presence of antibody specifically reactive with the polypeptide. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding OmpL1 or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

For purposes of the invention, the antibody which binds to OmpL1 of the invention may be present in various biological fluids and tissues. Any sample containing a detectable amount of antibodies to OmpL1 can be used. Normally, a sample is a liquid such as urine, saliva, cerebrospinal fluid, blood, serum and the like, or a solid or semi-solid such as tissue, feces and the like.

The monoclonal antibodies of the invention, directed toward OmpL1, are also useful for the in vivo detection of antigen. The detectably labeled monoclonal antibody is given in a dose which is diagnostically effective. The term "diagnostically effective" means that the amount of detectably labeled monoclonal antibody is administered in sufficient quantity to enable detection of Leptospira OmpL1 antigen for which the monoclonal antibodies are specific.

The concentration of detectably labeled monoclonal antibody which is administered should be sufficient such that the binding to those cells, body fluid, or tissue having OmpL1 is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the subject. The dosage of monoclonal antibody can vary from about 0.001 mg/m$^2$ to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140-250 key range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies of the invention can be used to monitor the course of amelioration of Leptospira associated disorder. Thus, by measuring the increase or decrease of Leptospira OmpL1 polypeptide or antibodies to OmpL1 polypeptide present in various body fluids or tissues, it would be possible to determine whether a particular therapeutic regiment aimed at ameliorating the disorder is effective.

The materials for use in the method of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a OmpL1 binding reagent, such as an antibody. A second container may further comprise OmpL1 polypeptide. The constituents may be present in liquid or lyophilized form, as desired.

The following examples are intended to illustrate but not limit the invention. While they are typical of those that might be used, other procedures known to those skilled in the art may alternatively be used.

EXAMPLES

The following examples describe the identification of OmpL1 as an important leptospiral OMP candidate. A comprehensive study of L. alstoni surface components is presented, including nonionic detergent extraction of the leptospiral outer membrane, surface immunoprecipitation, and freeze-fracture electron microscopy. The method by which the ompL1 gene was cloned and sequenced is described. Sequence analysis and homology studies are shown, further indicating that OmpL1 is an OMP. Southern hybridization and immunoblot studies show that OmpL1 is relevant to a broad range of pathogenic Leptospira, regardless of the species.

Example 1

TRITON X-114 NONIONIC DETERGENT EXTRACTION OF THE OUTER MEMBRANE

The approaches used to characterize surface components were designed to address problems inherent in the known fragility of the spirochetal outer membrane (OM). The first approach involved the use of the nonionic detergent Triton X-114 (TX-114) which has the useful characteristic of partitioning into hydrophobic and hydrophilic phases upon warming. Membrane proteins are hydrophobic and typically fractionate into the hydrophobic phase, while soluble, non-membrane proteins fractionate into the hydrophilic phase. Several lines of evidence suggested that 0.1% TX-114 selectively solubilized the leptospiral OM. TX-114 treatment reduced the leptospiral diameter with loss of discernable OM structure and resulted in essentially complete release of LLS. The TX-114 soluble fraction was free of periplasmic flagella as determined by immunoblot probed with cross-reactive antiserum specific for *T. pallidum* endoflagella. This finding represents the first demonstration of epitopic conservation between endoflagella of *T. pallidum* and Leptospira.

Extraction of *L. alstoni* using 0.1% TX-114 resulted in the solubilization of a number of proteins varying in molecular weight from greater than 100 kDa to less than 14 kDa. Roughly 16 proteins partitioned into the hydrophobic, detergent phase. Detergent phase proteins of 35-, 39-, and 66-kDa appeared to be unique to the virulent strain. By comparison, detergent phase proteins of 31-kDa (OmpL1) and 38-kDa appeared to be expressed in greater amounts in the attenuated strain. The virulent and attenuated strains contained similar amounts of the major detergent phase proteins with molecular weights of 41- and 44-kDa. The presence of LLS in leptospiral samples subjected to SDS-polyacrylamide gel electrophoresis was manifested by a characteristic pattern of bands upon either periodate-silver staining or immunoblotting. TX-114 studies demonstrated that leptospiral LLS partitioned exclusively into the hydrophobic phase, confirming that LLS is a hydrophobic, outer membrane component. This result is also consistent with the hydrophobic nature of the long-chain fatty acid component of LLS.

Example 2

SURFACE IMMUNOPRECIPITATION OF OUTER MEMBRANE COMPONENTS

The second approach used to identify surface components of *L. alstoni* was surface immunoprecipitation using antiserum raised to whole organisms. In order to avoid physical manipulation of the fragile spirochetes, a modification of the surface immunoprecipitation technique of Hansen, et al (*Infect. Immun.* 31:950–953, 1981), was used which involved addition of antiserum to a culture of intact, motile Leptospira in the log-phase of growth. The agglutinated Leptospira were then washed free of unbound antibody using low speed centrifugation (2,000×g) in order to avoid disruption of the outer membrane. The antigen-antibody complexes were solubilized in the Hansen solubilization buffer, and isolated using Staphylococcal protein A-Sepharose (CL-4B (Sigma)). Immunoblot of the immunoprecipitated material did not detect appreciable amount of the 35–36-kDa doublet endoflagellar protein, supporting the selectivity of the immunoprecipitation procedure for the identification of leptospiral surface components.

The surface immunoprecipitation procedure provided information corroborating the surface location of the 31-kDa (OmpL1), 41-kDa, and 44-kDa proteins. The 31-kDa (OmpL1) protein was present in significantly greater amounts in culture-attenuated *L. alstoni* than in virulent *L. alstoni*. The 41-kDa and 44-kDa proteins were present in similar amounts in the two strains. Surface immunoprecipitation results provided evidence demonstrating that LLS epitopes of *L. alstoni* have surface exposure on living cells; earlier radioimmunoprecipitation studies focused entirely on the surface exposure of protein epitopes.

Example 3

DETERMINATION OF OMP CONTENT BY FREEZE-FRACTURE ELECTRON MICROSCOPY

Suspensions containing approximately $4 \times 10^8$ viable spirochetes (100% motility), as determined by enumeration of 20 fields by dark-field microscopy (at least 200 total organisms), were centrifuged at 30,000×g to pellet the organisms. The pellets were suspended in 2 ml of 2% glutaraldehyde in 0.1M sodium cacodylate buffer (pH 7.4). After 15 min of fixation, 1 ml of the suspension was transferred to each of two 1.5-ml microfuge centrifuge tubes and the treponemes were pelleted by centrifugation at 14,000×g. The pellets were suspended in 50 µl of 20% glycerol in 0.1M sodium cacodylate buffer (pH 7.4). These manipulations were performed at ambient temperature (22° to 24° C.). From this suspension, 2-µl portions were placed on standard Balzars specimen holders (Balzars Co., Nashua, N.H.) The samples were frozen by immersion in liquid propane (−190° C.), using a guillotine-type device. The frozen samples were transferred under liquid nitrogen to the specimen state of a Balzars, 400K freeze-fracture apparatus precooled to −150° C. The frozen suspension of bacteria was fractured at −120° C. using a knife cooled at the temperature of liquid nitrogen. The fracture surface was immediately replicated with platinum-carbon at 45' and carbon at 90'. The replicas were floated in 3 to 4% sodium hypochlorite to bleach the organic material, washed three times in double distilled water, and placed on Formvar-coated freeze-fracture grids (Ted Pella Inc., Redding, Calif.). The grids were observed in a JEOL 100 CX II electron microscope operated at 80 kV. For each organism studied, a minimum of 50 fields was photographed and printed at a final magnification of ×100,000; typical fractured cells were chosen from these fields for determination of intramembranous particle density.

The outer membrane particle density of virulent and culture-attenuated *L. alstoni* serovar grippotyphosa was studied. The results were interesting in two respects: 1) Like other pathogenic spirochetes, this serovar of *L. alstoni* had a low OMP content relative to enteric gram-negative bacteria; and 2) comparison of virulent and attenuated *L. alstoni* revealed a direct correlation between expression of the 31-kDa protein (OmpL1) and integral membrane particle density.

Example 4

CLONING OF THE 31 KDA PROTEIN OmpL1

The weight of evidence from the different approaches used to study *L. alstoni* surface components led to the conclusion that the 31-kDa protein was the most promising OMP candidate. The fact that the amount of the 31-kDa protein present was not correlated with virulence does not diminish its importance because it would be the first membrane spanning spirochetal OMP to have been identified. The N-terminal amino acid sequence of the 31-kDa protein was obtained as follows. The surface immunoprecipitation procedure was used to generate a sample which was subjected to SDS-polyacrylamide gel electrophoresis, transferred to Trans-Blot PVDF Protein Sequencing Membrane (Bio-Rad, Richmond, Calif.), and submitted to the UCLA microsequencing facility. It was possible to determine the N-terminal 13-14 consecutive amino acids (SEQ ID NO:3) of the 31-kDa protein. Based upon the N-terminal amino acid sequence, two degenerate oligonucleotide probes were synthesized (SEQ ID NO:4 and 5)

tural gene consists of 960 bases encoding a protein of 320 amino acids. E. coli-like-35 (TTGCCG) and −10(TCCAAT) promoter regions are present upstream. An E. coli consensus ribosome-binding site (AGGAG) is present 6 bases upstream from the initiation codon. As expected for proteins to be exported beyond the inner membrane, the derived amino acid sequence begins with a 24 residue signal peptide represented by the shaded area in FIG. 1. There is a leader peptidase I cleavage site, the sequence of which is typical for procaryotic exported proteins in that there is an alanine at the −1 position. It is also notable that the amino acid sequence does not contain a concensus Leu-X-Y-Cys leader peptidase II cleavage site, indicating that OmpL1 is not a lipoprotein. To test whether or not this export signal is functional in E. coli, an Ssp I fragment containing the OmpL1 leader was

|  | -1- LYS | -2- —THR | -3- —TYR | -4- —ALA | -5- —ILE | -6- —VAL | -7- —GLY | -8- —PHE | -9- —GLY | -10- —LEU | -11- —GLN | -12- —LEU | -13- —ASP | -14- —ASN— |
|---|---|---|---|---|---|---|---|---|---|---|---|---|---|---|
| Oligo 1: | AAG A | —ACG A T C | —TAT C | —GCG A T C | —ATA T C | —GTG A T C | —GG |  |  |  |  |  |  |  |
|  |  |  |  |  |  |  | Oligo 2: | TTT C | —GGG A T C | —CTG T A T | —CAA G | —CTG T A T | —GAT C | —AA |

L. alstoni genomic DNA was prepared by the method of Yelton, D. B., and N. W. Charon, (Gene, 28:147, 1984). The oligonucleotide probes were end-labeled with gamma $^{32}$P-ATP, and independently identified a 2.5 kb Eco RI fragment by Southern hybridization of the L. alstoni genome. An Eco RI genomic digest was separated by agarose gel electrophoresis. Fragments with a size range of 2.1–2.8 kb generated by restriction endonucleases, representing 10% of the total Leptospira DNA, were removed and gel purified. These DNA fragments were ligated into the Lambda Zap II vector (Stratagene). The oligonucleotide probes were used to independently screen a library of 4800 plaques. The size of the Leptospira genome, is roughly five megabases (Baril, et al FEMS Microbiol Lett., 71:95–100, 1990). The bacteriophage lambda library represented about 10% of the total genome, or 500,000 base pairs. The expected frequency of positive plaques would be fragment size/genome fraction= 2500/500,000=0.25%. Based upon this calculation, hybridization was expected to 4800×0.25%=12 plaques. Both oligonucleotide probes hybridized to the same 18 plaques. Six positive plaques were picked, replated, and reprobed in order to purify phage bearing the hybridizing DNA fragment. Purified phage were amplified and converted to pBluescript SK-plasmid form by in vivo excision and recircularization. All six pBluescript plasmids obtained in this way contained the same 2.5 kb insert. A restriction map of the insert was constructed. Southern hybridization using the oligonucleotide probes was performed, localizing the area of hybridization to a 122 bp fragment near the Nde I site.

Example 5

SEQUENCE ANALYSIS FOR ompL1

Restriction fragments were subcloned into pBluescript for double-stranded DNA sequencing using the Sequenase reaction with the T7 forward and T3 reverse primers. The DNA sequence was analyzed using the DNA Strider 1.0 program. An intact open reading frame was found beginning 770 bases in from the upstream Eco RI site. The ompL1 struccloned into the Sma I site of the polylinker of the alkaline phosphatase expression vector pMG and transformed into IT41, a strain of E. coli with a temperature sensitive leader peptidase 1 mutation (Inada, et al., J. Bacteriol., 171:585–587, 1989). The resultant OmpL1-PhoA fusion protein was exported to the periplasm resulting in blue colonies on agar containing the alkaline phosphatase substrate XP (bromo-chloro-indolyl-phosphate). Cleavage of the OmpL1-PhoA fusion protein was demonstrated at the permissive temperature of 32° C., but not at the restrictive temperature of 37° C., confirming sensitivity of OmpL1 to E. coli leader peptidase 1 cleavage. Immediately following the leader peptidase 1 cleavage site was a sequence of 13 amino acids that agreed exactly with the first 13 amino acids of the N-terminal amino acid sequence obtained from the native protein. The 296 amino acid mature protein has a calculated molecular weight of approximately 31,000 daltons, which is similar to that observed experimentally. The hydrophobicity plot shows an N-terminal peak of 0.75, corresponding to the leader peptide. There are no other regions with a hydrophobicity score of greater than 0.65, consistent with the idea that the ompL1 gene does not encode an inner membrane protein. Downstream of the termination codon (TAA) is an inverted repeat, which might function as a rho-independent transcription terminator, extending from nucleotides 997 to 1027.

The OmpL1 sequence contains ten stretches of amphipathic beta-sheet structure consistent with OMP transmembrane segments. On the basis of the primary amino acid sequence data it is possible to propose a topological model of OmpL1 which conforms to structural rules based upon the topology of well-defined porins of gram-negative bacteria. Each of the transmembrane segments is ten amino acids in length, and within these ten transmembrane segments there are no exceptions to the alternating hydrophobic amino acid rule. The amino acids in the transmembrane segments are shown in a staggered array with the hydrophobic, membrane-facing residues on the right side of the array. Some of the transmembrane segments are reflected as peaks on the beta-moment plot, which is designed to identify areas where hydrophobic and hydrophilic amino acids alternate and is useful in predicting OMP membrane spanning sequences (Vogel, et al, *J. Mol. Biol.*, 190:191–199, 1986). The five surface-exposed loops of varying length contain segments of high surface probability. The four periplasmic loops are typical of OMPs in that they are short, and contain amino acids, such as proline (P), glucine (G), serine (S), and asparagine (N), which are turn promoters (Jeanteur, et al., *Molec. Microbiol* 5:2153–2164, 1991).

The carboxy-terminal ten amino acids of OmpL1 revealed an alternating pattern of hydrophobic amino acids which is characteristic of gram-negative OMPs. Of particular interest is the fact that there is a histidine at the -3 position. Histidine is found at this position in the carboxy-terminal transmembrane segment of class 1 (Nmp1) and class 2 (Nmp2) porins of *Neisseria meningitidis*, as well as the pI porin of *Neisseria gonorrheae* (Jeanteur, et al., *Molec. Microbiol.*, 5:2153–2164, 1991). Using the Gap Alignment program (University of Wisconsin, Genetics Computer Group), set at a gap width of 3.0, alignment of the entire OmpL1 sequence with that of Nmp1 revealed that 21% of the amino acids were identical and another 45% were similar. Pairwise alignment of OmpL1 with a variety of other proteins indicated that OmpL1 is more homologous to Nmp1 than to OMPs of *E. coli* (such as LamB, OmpF, or PhoE). OmpL1 was more homologous to OMPs than to periplasmic proteins of *E. coli* (such as AraF or beta-lactamase). The gap alignment score of OmpL1 with these proteins is shown in brackets: Nmp1 [113.5], LamB [107.7], PhoE [104.8], AraF [95.7], and beta-lactamase [95.5]. Scores of pairwise alignment have been used to assess relative homology of porins (Gerbl-Reiger, S., et al., *J. Bacteriol*, 173–2196–2205, 1991). Gap alignment of OmpL1 with Nmp1 demonstrated homology in areas corresponding to known Nmp1 transmembrane segments. Neisserial porins show greatest sequence conservation in their transmembrane segments (Van der Ley, P., et al., *Infect. Immun.* 59:2963–2971, 1991). Transmembrane segments (TMSs) #6, #7, #8, #9, #11, and #16 of Nmp1 aligned with the OmpL1 sequence in a pattern such that most of the alternating hydrophobic residues (*) of the Nmp1 transmembrane segments were identical (I) or similar (:) to those in OmpL1 (FIG. 2).

Example 6

SOUTHERN HYBRIDIZATION STUDIES

Figure 3B:
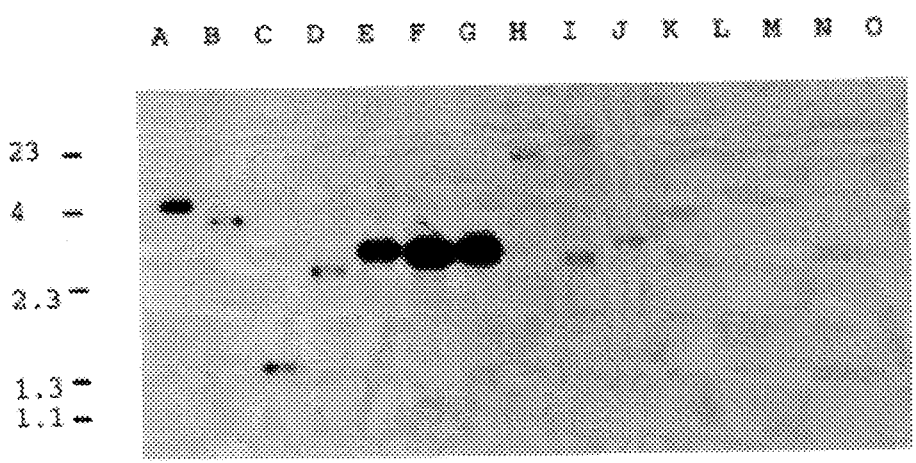
FIG. 3B shows a Southern blot using ompL1 as a probe to detect the gene in pathogenic and non-pathogenic Leptospira (high stringency).

There is a strong correlation between Leptospira pathogenicity and the presence of the ompL1 gene. Southern hybridization studies were performed as follows. The ompL1 gene has a unique Nde I site two codons after the leader peptides cleavage site is encoded. There is also a unique Pvu I site near the end of the structural gene. The 834 base pair Nde I-Pvu I fragment, encoding 94% of the mature protein, was labeled with alpha $^{32}$P-dCTP by the random priming method and used to probe Eco RI genomic digests of eleven pathogenic and four nonpathogenic Leptospira strains. FIG. 3A shows the results after washing at medium stringency in 2× SSC at 55° C. A single copy of the gene was present in all the tested strains of pathogenic Leptospira. The gene was not present in nonpathogenic strains of Leptospira. FIG. 3B shows the results after washing at high stringency in 0.1× SSC at 55° C. The most homologous ompL1 genes are found in other *L. alstoni* serovars tested.

Example 7

CLONING OF THE ompL1 GENE INTO THE pRCET EXPRESSION VECTOR

The pBluescript plasmid containing the ompL1 gene was digested with Nde I, filled in the Klenow to generate blunt ends, and then digested with Eco RI. The resulting 1600 base pair DNA fragment encoding essentially the entire mature OmpL1 protein was isolated by agarose gel electrophoresis, and ligated into pRSET (Invitrogen, San Diego, Calif.) digested with Sma I and Eco RI. The resulting construct, pRSET-ompL1, encodes a fusion protein containing a 41 amino acid His6 binding site at the amino terminus of OmpL1. The six histidines allow for pH-dependent affinity purification of the fusion protein on a nickel resin column to the exclusion of *E. coli* proteins. The pRSET fusion protein is under T7 promoter control. After transformation of pRSET-ompL1 into *E. coli* DH5α, milligram quantities of the His6-OmpL1 fusion protein were produced in the presence of isopropyl-β-D-thiogalactoside (IPTG, Sigma). Addition of rifampicin (Sigma) one hour after IPTG induction enhanced His6-OmpL1 production relative to *E. coli* proteins. The bulk of the *E. coli* host proteins were released after several freeze-thaw cycles in lysis buffer, while >90% of the insoluble pellet consisted of the His6-OmpL1 fusion protein.

Example 8

IMMUNIZATION OF RABBITS WITH PURIFIED OmpL1

The His6-OmpL1 fusion protein was separated from other insoluble materials by SDS-PAGE. The His6-OmpL1 band containing 50 micrograms of protein was cut out of the acrylamide gel, dessicated, ground to powder, mixed with Freund's complete adjuvant and inoculated subcutaneously and intramuscularly into a New Zealand White male rabbit. Additional His6-OmpL1 fusion protein was solubilized in 6M guanidine and purified over the nickel resin column and dialyzed in 10mM Tris, pH 8.0. The secondary immunization was given six weeks after the primary immunization using roughly 50 micrograms of purified His6-OmpL1 fusion protein in Freund's incomplete adjuvant. The rabbit was bled two weeks after the secondary immunization. The post-boost antiserum reacted only with the 31-kDa antigen on immunoblots of whole *L. alstoni* separated by SDS-PAGE. Immunoblots of *L. alstoni* fractioned with TX-114 revealed reactivity with the 31-kDa OmpL1 antigen in the whole organism and detergent phase, but not the aqueous phase or insoluble pellet.

Example 9

SURFACE LOCALIZATION WITH IMMUNOELECTRON MICROSCOPY

Having obtained a highly specific immunological reagent for localization studies, preliminary immunoelectron microscopy experiments were conducted. A 20 µl suspension of $10^7$ *L. alstoni* was added to 0.5 ml of heat-inactivated anti-OmpL1 antiserum or preimmune serum from the same rabbit and incubated for one hour with mixing. The bacteria were fixed for 30 minutes by addition of 250 µl of 0.75% glutaraldehyde in 100 mM cacodylate buffer, pH 7.0. The bacteria were washed, applied to electron microscopy grids, and probed with protein G-colloidal gold (10 nm particles). A low level of specific binding to the outer membrane of *L. alstoni* was observed. With preimmunization serum, one particle per twenty organisms was observed, whereas with anti-OmpL1 antiserum eight particles per twenty organisms was observed. A low level of binding was anticipated because of the paucity of leptospiral OMPs.

Example 10

EXPRESSION OF OmpL1 WITH THE pTrc 99A EXPRESSION VECTOR

The His6 fusion protein is well suited for purification, but is not appropriate for immunoblotting studies because of the potential for background reactivity to the 41 additional amino acids containing the His6 binding site. Preimmune sera from one of the rabbits reacted with the His6-OmpL1 fusion protein, but not with native OmpL1. A Bgl II-Hind II fragment was isolated from the pRCET-ompL1 vector by gel electrophoresis and cloned into the pTrc99A expression vector (Pharmacia) which had been reading frame adjusted with a 10-mer Nco I linker. The pTtrc99A-ompL1 construct, transformed into *E. coli* DH5α expresses the entire mature OmpL1 protein, plus a start methionine and only five additional amino acids supplied by the vector. *E. coli* DH5α containing the original pTrc99A vector served as a negative control. Bacterial proteins were separated by SDS-PAGE and transferred to nitrocellulose, and probed with antisera from rabbits immunized with a variety of pathogenic Leptospira strains (antisera supplied by Dr. Arnold Kaufmann, Centers for Disease Control, Atlanta). Reactivity to OmpL1 was demonstrated with antisera to *L. interrogans*, serovars icterohaemorrhagiae, pomona, and bratislava, *L. alstoni*, serovars grippotyphosa and fortbragg, *L. santarosai*, serovars bakeri and canalzonae, and *L. weilii*, serovar celledoni. This indicates that OmpL1 is not only expressed, but also antigenically conserved among pathogenic Leptospira, a feature that would make it an excellent vaccine candidate.

The foregoing is meant to illustrate, but not to limit, the scope of the invention. Indeed, those of ordinary skill in the art can readily envision and produce further embodiments, based on the teachings herein, without undue experimentation.

SUMMARY OF SEQUENCES

SEQUENCE ID NO. 1 is the nucleotide and deduced amino acid sequence of ompL1.

SEQUENCE ID NO. 2 is the deduced amino acid sequence of OmpL1.

SEQUENCE ID NO. 3 is the amino acid sequence of the N-terminus of OmpL1.

SEQUENCE ID NO. 4 is the nucleotide sequence for an oligonucleotide probe for OmpL1.

SEQUENCE ID NO. 5 is the nucleotide sequence for an oligonucleotide probe for OmpL1.

SEQUENCE ID NO. 6 is the amino acid sequence of NMP1.

SEQUENCE ID NO. 7 is the amino acid sequence of PepL (or OmpL1).

We claim:

1. An isolated polynucleotide sequence which encodes the amino acid of SEQ ID NO:2.

2. The polynucleotide of claim 1, wherein the polynucleotide is the sequence as set forth in SEQ ID NO:1.

3. The polynucleotide sequence of claim 1, wherein the polynucleotide is DNA.

4. The polynucleotide sequence of claim 1, wherein the polynucleotide is RNA.

5. A recombinant expression vector containing the polynucleotide of claim 1.

6. The expression vector of claim 5, wherein the vector is a plasmid.

7. A host cell transformed with the expression vector of claim 5.

8. The host cell of claim 7, wherein the cell is a prokaryote.

9. The prokaryote of claim 8, which is *E. coli*.

10. The host cell of claim 7, wherein the cell is a eukaryote.

11. A method of producing OmpL1 polypeptide which comprises:

a. transforming a host cell with an expression vector containing in operable linkage, the polynucleotide of claim 1; and b. expressing the polynucleotide in the host cell.

12. The method of claim 11, which further comprises isolating the OmpL1 polypeptide.

13. The method of claim 11, wherein the host is a prokaryote.

14. A kit useful for the detection of OmpL1 polynucleotide, the kit comprising a carrier means with at least two containers, wherein the first container contains a nucleic acid which encodes the amino acid sequence of SEQ ID NO:2 and wherein a second container contains a label for detection of nucleic acid for identification of the presence of OmpL1 polynucleotide.

* * * * *

UNITED STATES PATENT AND TRADEMARK OFFICE
CERTIFICATE OF CORRECTION

PATENT NO. : 5,658,757

DATED : 8/19/97

INVENTOR(S) : David A. Haake et al.

It is certified that error appears in the above-identified patent and that said Letters Patent is hereby corrected as shown below:

At column 1, line 7, after "AI-21352" please insert --,AI 29733 and AI 12601--.

Signed and Sealed this

First Day of June, 1999

Attest:

Attesting Officer

Q. TODD DICKINSON

Acting Commissioner of Patents and Trademarks